US00PP30258P2

(12) United States Plant Patent
Hansen

(10) Patent No.: US PP30,258 P2
(45) Date of Patent: Feb. 26, 2019

(54) ***PULMONARIA* PLANT NAMED 'TWINKLE TOES'**

(50) Latin Name: ***Pulmonaria* hybrid**
Varietal Denomination: Twinkle Toes

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,093

(22) Filed: Feb. 1, 2018

(51) Int. Cl.
*A01H 5/02* (2018.01)

(52) U.S. Cl.
USPC ..... Plt./473
CPC ..... *A01H 5/02* (2013.01)

(58) Field of Classification Search
USPC ..... Plt./473
CPC ..... A01H 5/02
See application file for complete search history.

(56) References Cited

PUBLICATIONS http://www.gardencentermag.com/article/walters-gardens-december-2017/; Walters Gardens Variety Guide; Dec. 18, 2017; 3 pages.*

* cited by examiner

*Primary Examiner* — Kent L Bell

(57) ABSTRACT

A new and distinct hybrid of *Pulmonaria* characterized by silver spotting on medium green foliage, medium pink flower buds on upright, highly branched stems, flowers that open to a dainty light periwinkle blue petals from outright to slightly drooping campanulate flowers. The new plants show excellent vigor and good mildew resistance.

1 Drawing Sheet

Botanical denomination: *Pulmonaria* hybrid.
Variety designation: 'Twinkle Toes'.

BACKGROUND OF THE INVENTION

The present invention relates to a new and distinct cultivar of *Pulmonaria* and given the cultivar name of 'Twinkle Toes'. *Pulmonaria* is in the family Boraginaceae. The new cultivar originated from a cross under the direction of the inventor in the greenhouses of a wholesale perennial nursery in Zeeland, Mich., USA on Mar. 11, 2013 between an unpatented, proprietary, experimental plant that is presumed to be a tetraploid converted plant of *Pulmonaria* 'Roy Davidson' (not patented) as the seed parent, and an unpatented, unreleased, proprietary wild collected specimen of *Pulmonaria officinalis* with the acquisition code 12-HH-BC-043-06 (not patented), as the pollen parent. The new plant was evaluated at the same nursery beginning in 2014 as a single select seedling using the breeder code 13-116-1.

The new plant was initially asexually propagated at the same nursery in the summer of 2015 by division of the rhizome and followed by plant tissue culture of the shoot tip. The result plants have shown themselves to be stable and true to type in successive generations of asexual propagation by division at the same nursery in Zeeland, Mich. and also through shoot tip tissue culture.

No plants of *Pulmonaria* 'Twinkle Toes' have been sold, under this or any name, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

SUMMARY OF THE INVENTION

*Pulmonaria* 'Twinkle Toes' is distinct from all other lungwort plants known to the inventor by the following combined traits:

1. Medium pink flower buds on upright highly-branched stems in mid-spring
2. Pink flower buds open to dainty light periwinkle blue outright to slightly drooping campanulate flowers on flattened panicle;
3. Medium green foliage with prominent silver spotting on both cauline leaves and basal leaves arising after flowering;
4. Excellent vigor producing compact mounded habit; and
5. Foliage shows good mildew resistance.

Compared with the female parent, the new plant has darker pink flower buds, the foliage is more ovate and less oblanceolate. Compared with the male parent, the new cultivar has a more compact habit, more floriferous and flowers are a lighter shade of blue. 'Roy Davidson' (not patented) has slightly lighter flowers. 'Trevi Fountain' U.S. Plant Pat. No. 13,047 has more purplish flowers. 'Baby Blue' U.S. Plant Pat. No. 13,682 has much lighter blue flowers when open and deeper pink flower buds. 'Smokey Blue' (not patented) has slightly more purplish tint to the flowers and the foliage is larger with less distinct silver spotting.

BRIEF DESCRIPTION OF THE DRAWING

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photographs are of a three-year-old plant growing in a partially shaded trial garden in Zeeland, Mich.

DETAILED PLANT DESCRIPTION

Figure 1:
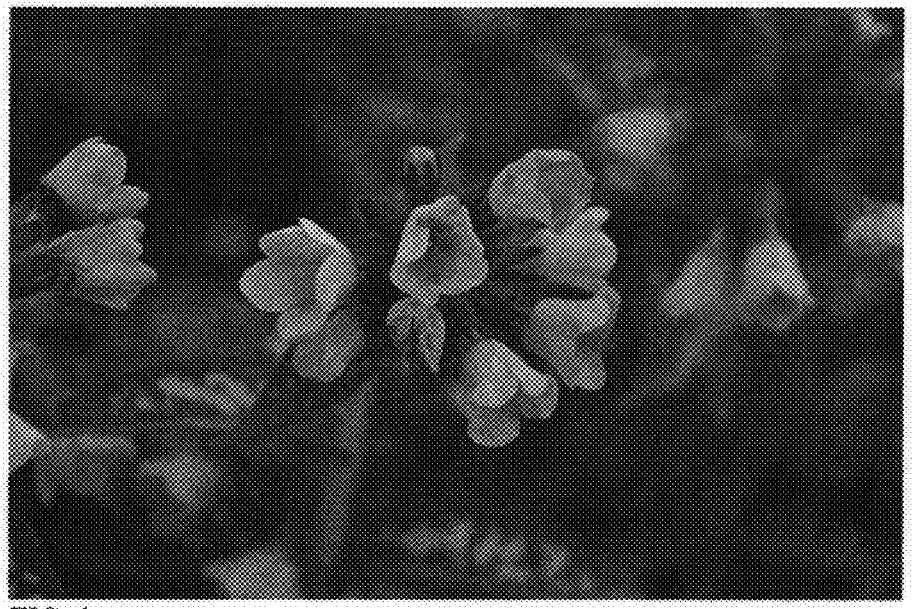
FIG. 1 shows a close-up of flowers and buds of the new plant.
Figure 2:
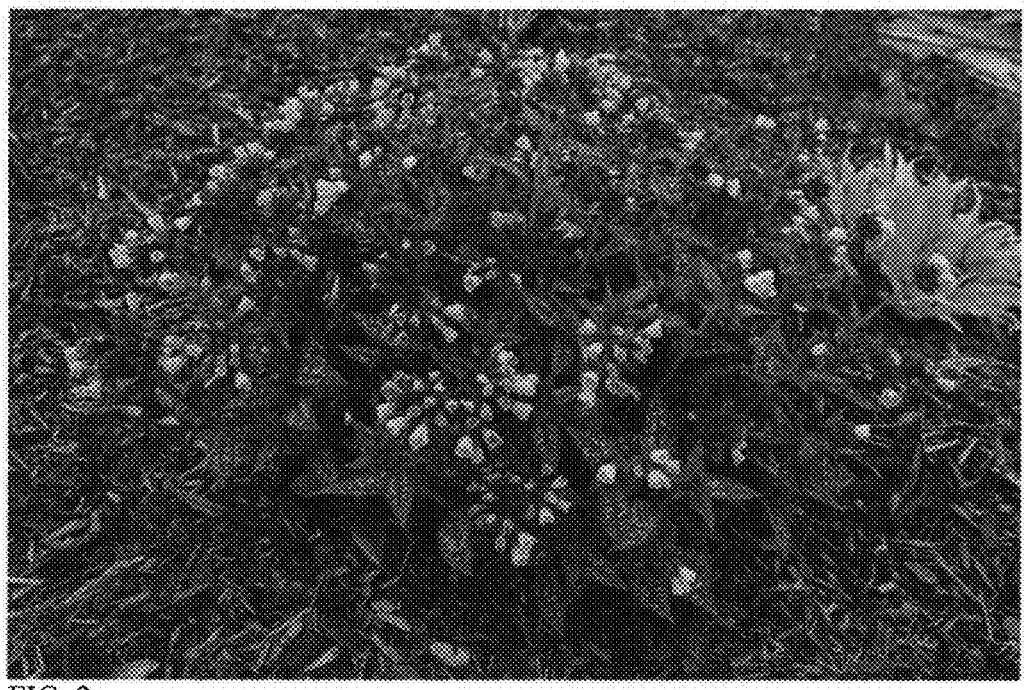
FIG. 2 shows the spring foliage and flowering habit of the new plant.

The following is a detailed description of three-year-old plants of the new cultivar as grown outdoors in a partially shaded trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with The 2001 edition of The Royal Horticultural Society Colour Chart except where general color dictionary terms are used.

Parentage: Plant presumed to be a tetraploid converted plant of *Pulmonaria* 'Roy Davidson' as the female or seed parent, and an unpatented proprietary wild collected specimen of *Pulmonaria officinalis* with the acquisition code 12-HH-BC-043-06 (not patented) as the male or pollen parent;

Plant habit: Herbaceous, perennial forming low, multi-stemmed, flowering mound in spring followed in summer producing a clumping basal rosette;

Size: With spring flowering 44.0 cm wide and 28.0 cm tall; summer foliage size 60.0 cm wide and 28.0 cm tall;

Vigor: Excellent; produces rooted plantlet in tissue culture in about 18 to 20 days; fills a 3.8 liter container in about 10 weeks from tissue cultured plug;

Propagation: Division of the crown or tissue culture;

Roots: Fleshy, to about 3.0 mm thick near white depending on soil type;

Leaf: Developing prior to cymes dehiscing; simple; oblanceolate; pubescent to hispid abaxial and adaxial; apex acute; base attenuate, semi-clasping; margin entire, ciliolate; with spots on adaxial surface between 0.5 mm and 4.0 mm in diameter;

Leaf size (basal rosette): To about 19.0 cm long and 5.9 cm wide at midpoint; average about 17.0 cm long and 5.2 cm wide;

Cauline leaf: Oblanceolate; pubescent to hispid abaxial and adaxial; acute apex; base attenuate and semi-clasping; margin ciliolate and entire; with spots on adaxial surface between 0.5 mm and 4.0 mm diameter; to 8.5 cm long and 20.0 mm wide decreasing distally to 3.0 cm long and 14.0 mm wide; average about eight cauline leaves per stem below flowers; cauline leaves and stems not persistent, drying after seed production;

Leaf color (basal and cauline): Abaxial between RHS 138A and RHS 138B; adaxial nearest RHS 137A with spots covering approximately 25% of leaf between RHS 193B and RHS 193C;

Venation: Pinnate; only abaxial and adaxial midrib distinct; hispid to pubescent abaxial and adaxial;

Vein color: Abaxial midrib between RHS N144A and RHS 145A; adaxial midrib nearest RHS N144A;

Petiole description: Concavo-convex; scabrous;

Petiole size: To about 17.0 cm long and 11.0 mm wide at base; average about 16.0 cm long and 10.0 mm wide;

Petiole color: Adaxial and abaxial margin nearest RHS 137C; adaxial center nearest 145C; abaxial longitudinal center nearest RHS 145C in basal portion, distally blend between RHS 160C and lighter than RHS 146D;

Inflorescence: Terminal branched cyme; average about 38 flowers per cyme; average about 34.5 inflorescences per plant;

Flowering period: Beginning about mid-April and continuing for three weeks;

Flower longevity: Individual flowers open for about four days;

Flower fragrance: None detected;

Peduncle: Terete; hispid; about 27 cm long, about 5.0 mm diameter at base; upright;

Peduncle color: Nearest RHS 145A;

Pedicel: Terete; variable length to about 8.0 mm and about 1.5 mm diameter, hispid; color nearest RHS 146B;

Flower bud: Clavate; basal tube 8.0 mm long and 4.5 mm wide, with swollen distal portion about 8.0 mm long and 6.0 mm diameter where extends beyond calyx.

Flower bud color: Tight buds closer to RHS 63C than RHS 63B; one day prior to opening calyx base nearest RHS 155A and distal calyx nearest RHS N78D with exposed petal nearest RHS 65A distally and RHS 62A where petals fused;

Flower: Campanulate, actinomorphic, forming funnelform corolla; size 19.0 mm long and 12.0 mm wide;

Petals: Typically five, rarely six; fused in basal 15.0 mm with rounded apices; margins entire; glabrous abaxial and adaxial except for adaxial tufts of hairs about 2.0 mm long at opening of tube about 8.0 mm from base;

Petal color: Abaxial tube basal 5.0 mm nearest RHS 155D, distal 8.0 mm between RHS 97A and RHS 97B with portion between base and distal nearest RHS 84A; adaxial tube base nearest RHS 155D, distal portion between RHS 97A and RHS 97B with middle portion nearest RHS 84A;

Calyx description: Fused at base, tubular campanulate; about 13.0 mm long and 6.0 mm across at apex;

Sepals: Five; apices narrowly acute; fused in basal about 8.0 mm; hispid abaxial and hispidulous adaxial;

Sepal color: Abaxial nearest RHS 137C with tinting of nearest N187A, adaxial between RHS 137C and RHS 144A;

Gynoecium: One; pistil to about 13 mm long;

Ovary: Partially inferior, four-chambered; globose to about 1.5 mm diameter; color nearest RHS 144C;

Style: Terete, glabrous; about 1.0 mm long and less than 1.0 mm diameter at base; color nearest RHS 155D;

Stigma: Globose to about 0.7 mm diameter; color nearest RHS 155D;

Androecium: Five;

Filament: Entirely adnate to inner petal; color white, lighter than RHS 155D;

Anther: Fused to petal; introrse; dorsifixed; longitudinal; oblong about 2.0 mm long and 0.5 mm diameter, color nearest RHS N186A;

Pollen: Abundant; color RHS 155D;

Seed: Type: not observed;

Resistance to pest and diseases: *Pulmonaria* 'Twinkle Toes' has not shown any resistance or susceptibility beyond that common to other lungwort.

Hardiness: The new plant is hardy from at least USDA hardiness zones 3 through 9.

I claim:

1. A new and distinct cultivar of *Pulmonaria* plant named 'Twinkle Toes' as herein described and illustrated.

* * * * *